United States Patent [19]

Taylor et al.

[11] Patent Number: 4,680,145

[45] Date of Patent: Jul. 14, 1987

[54] PROCESS FOR PRODUCING DIPEROXOIC ACIDS

[75] Inventors: Keith M. Taylor, Ballwin; Liou-Liang Horng, Clayton; Timothy K. Hirzel, St. Louis, all of Mo.

[73] Assignee: Monsanto Company, St. Louis, Mo.

[21] Appl. No.: 891,825

[22] Filed: Aug. 1, 1986

Related U.S. Application Data

[63] Continuation of Ser. No. 646,720, Sep. 4, 1984.

[51] Int. Cl.$^4$ ............................................ C07C 178/00
[52] U.S. Cl. ................................................ 260/502 R
[58] Field of Search ................................... 260/502 R

[56] References Cited

U.S. PATENT DOCUMENTS 2,813,896 11/1957 Krimm ............................ 260/502 R
4,172,086 10/1979 Berkowitz ....................... 260/502 R Primary Examiner—Howard T. Mars
Assistant Examiner—Bruce D. Gray
Attorney, Agent, or Firm—R. Loyer

[57] ABSTRACT

Substituted-butanediperoxoic acids are produced by peroxidizing substituted succinic anhydride in a strong acid reaction medium in the presence of a reaction modifier. Product throughput is improved and product recovery is enhanced. The substituted-butanediperoxoic acids are particularly useful as bleaching agents.

12 Claims, No Drawings

PROCESS FOR PRODUCING DIPEROXOIC ACIDS

This is a continuation of application Ser. No. 646,720 filed Sept. 4, 1984.

This invention relates to the production of substituted-butanediperoxoic acids. More particularly, it relates to a process for producing substituted-butanediperoxoic acids by peroxidizing substituted succinic anhydrides in a strong acid reaction medium in the presence of a reaction modifier.

BACKGROUND OF THE INVENTION

Diperoxoic acids are useful as bleaching agents, oxidizing agents, disinfecting agents, and the like.

Methods of preparing various classes of diperoxoic acid are known. U.S. Pat. No. 2,377,038 issued May 29, 1945 to J. S. Reichert et al discloses a process for preparing organic peracid by reacting an anhydride of a carboxylic acid and an alkaline solution of an inorganic peroxygen compound in an aqueous medium at a pH of 8.0–11.0. U.S. Pat. No. 2,813,896 issued Nov. 19, 1957 to K. Krimm discloses a process for preparing organic peracids by reacting monocarboxylic and dicarboxylic aliphatic, cycloaliphatic and aromatic acids and acid anhydrides with aqueous hydrogen peroxide solution in sulfuric acid using such amounts that $H_2SO_4$ and $H_2O$ are at the rate of at least 1 mole to 6 moles at the end of the reaction. U.S. Pat. No. 3,655,738 issued Apr. 11, 1972 to D. R. Nelson discloses the preparation of diperphthalic acids by the reaction of phthalic acid in the form of finely divided particles having a dimension below 0.1 millimeter and hydrogen peroxide in an alkane sulfonic acid medium. U.S. Pat. No. 4,172,086 issued Oct. 23, 1978 to S. Berkowitz discloses an improved process for the manufacture of a peroxycarboxylic acid prepared by the oxidation of a fatty acid with an excess of hydrogen peroxide in the presence of a strong acid catalyst by intimately dispersing throughout the reaction mixture a sufficient amount of an inert, water-immiscible solvent for the peroxycarboxylic acid to selectively remove from the aqueous phase the peroxycarboxylic acid as it is formed. U.S. Pat. No. 4,233,235 issued Nov. 11, 1980 to J. B. Camden et al discloses a process for making aliphatic diperoxyacids having 8 to 16 carbon atoms by continuously adding a dibasic acid of the formula $HOOC-(CH_2)_n-COOH$, sulfuric acid, hydrogen peroxide and water to a reactor and continuously withdrawing the diperoxyacid formed to maintain a constant resident time for the reactants in the reactor. Similarly, U.S. Pat. No. 4,244,884 issued Jan. 13, 1981 to J. P. Hutchins et al relates to Camden et al and discloses a continuous process with two recycling loops.

U.S. application Ser. No. 490,591 filed on May 2, 1983 by J. M. Mayer, said application being owned by the owner of the present application, discloses substituted-butanediperoxoic acid bleaching agents. The preparation of the substituted butanediperoxoic acids shown in Ser. No. 490,591 is by the addition of hydrogen peroxide to a stirred mixture of substituted succinic anhydride and methanesulfonic acid. U.S. application Ser. No. 531,103 filed on Sept. 12, 1983 by H. R. Alul, also owned by the owner of the present application, discloses a process for making substituted-butanediperoxoic acids by reacting substituted succinic anhydride with a mixture of concentrated sulfuric acid and hydrogen peroxide.

Although these methods of preparing substituted-butanediperoxoic acids are effective it has now been found that these processes suffer the disadvantage of forming fine crystals of the substituted-butanediperoxoic acid product which gels the reaction mixture. The formed gel requires substantial increase in energy to agitate the reaction mixture, an increase in reactor size to accomodate the increased volume of the gel and prolonged production and product recovery periods. It has now been found that these disadvantages are overcome by using a reaction modifier.

SUMMARY OF THE INVENTION

These and other advantages of the present invention are achieved by a process which comprises reacting a substituted succinic anhydride with hydrogen peroxide in a strong acid reaction medium in the presence of a reaction modifier.

DETAILED DESCRIPTION OF THE INVENTION

In accordance with this invention the production of substituted-butanediperoxoic acids by reacting hydrogen peroxide with substituted succinic anhydride precursor in a strong acid reaction medium is conducted in the presence of a water-immiscible reaction modifier. The presence of the reaction modifier prevents the formation of a gelled reaction mixture and permits more efficient agitation of the reaction mixture, increased production rates, more efficient hydrogen peroxide usage and enhanced product recovery.

The substituted-butanediperoxoic acids made in accordance with the present invention are particularly useful as bleaching agents as more fully described in U.S. Ser. No. 490,591 filed on May 2, 1983 by J. M. Mayer, herein incorporated by reference.

The substituted butanediperoxoic acids can be represented by the general formula:

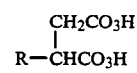

wherein R is alkyl of 6 to 18 carbon atoms or phenyl.

The substituted succinic anhydride precursor employed in the present process can be represented by the general formula:

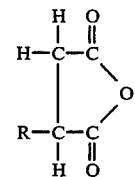

wherein R is alkyl of 6 to 18 carbon atoms or phenyl.

The reaction modifier employed in accordance with the present invention is substantially inert to chemical reaction under the process conditions and does not significantly change the liquid phase reaction process.

Suitable reaction modifiers are essentially water-immiscible hydrocarbons such as aliphatic, cycloaliphatic and aromatic hydrocarbons and halogenated hydrocarbons which do not react with hydrogen peroxide, strong acids, the succinic anhydride precursor or the diperoxoic acid product. Halogenated hydrocarbons are preferred reaction modifiers, for example, dichloromethane, trichloromethane, dichlorofluoromethane, 1-chloro-2-fluoroethane, 1,1-dichloroethane, 1,1,2-trichloro-1,2,2-trifluoroethane, 2-chloropropane, chlorobenzenes and the like. Particularly preferred are halogenated hydrocarbons having a boiling point in the range of about 5° to about 100° C., more preferably in the range of about 25° to about 65° C., such as methylene chloride, chloroform, 1,1-dichloroethane, 1 chloro-2-fluoroethane, 1,1,2-trichloro-1,2,2-trifluoroethane, 2-chloropropane and the like.

The quantity of the reaction modifier employed in the present process is substantially less than required to dissolve the substituted-butanediperoxoic acid product which upon formation precipitates in the reaction mixture to form a fluid slurry. It is advantageous to employ about 0.25 ml to about 2 ml or more, preferably about 0.75 ml to about 1.25 ml of the reaction modifier per gram of the substituted succinic anhydride precursor which is essentially soluble in the strong acid reaction medium. In this manner, the presence of the reaction modifier prevents the formation of a gelled reaction mass, promotes efficient reaction times and highly efficient product recovery in good yields.

Various water soluble strong acids can be employed as the reaction medium in the present process. For example, sulfuric acid, sulfuric acid plus up to about 30% oleum, sulfonic acids, such as methanesulfonic, ethanesulfonic, butanesulfonic, fluoromethanesulfonic, trifluoromethanesulfonic acids and the like, can be used as the strong acid reaction medium. Sulfuric acid and methane sulfonic acid are preferred, particularly sulfuric acid. The substituted succinic anhydride precursor is soluble in the reaction medium. The acid concentration of the sulfuric acid reaction medium is important. Particularly good results are obtained using an aqueous reaction medium in which the sulfuric acid is in the range of about 75% to about 90%, preferably about 80% to about 86%, by weight of the aqueous reaction medium, including the water contributed by the aqueous hydrogen peroxide reactant initially charged.

The hydrogen peroxide reactant employed in the present process can be commercially available hydrogen peroxide of various concentrations such as 30%, 50% or 70% $H_2O_2$. Preferably, the higher concentrations, consistent with good safety and handling practices, are employed. Particularly good results can be obtained employing 50% $H_2O_2$ as the peroxidizing reactant.

The substituted succinic anhydride precursors employed in accordance with the present invention are available compounds and can be prepared by techniques known to those skilled in the art. For example, alkyl-substituted succinic anhydride can be prepared by the hydrogenation of alkenyl succinic anhydride prepared by the reaction of maleic anhydride with olefins. See, for example, U.S. Pat. No. 3,412,111 issued Nov. 19, 1968 to P. G. Irwin et al. Preferred substituted succinic anhydride reactants are $C_{8-12}$ alkyl-substituted succinic anhydride wherein the alkyl substituent is, for example, octyl, decyl or dodecyl. If desired, mixtures of substituted succinic anhydrides can be used to provide mixtures of substituted-butanediperoxoic acids, for example, a mixture of octyl- and decylbutanediperoxoic acids.

In the process of the present invention, it is advantageous to use a quantity of the strong acid to provide a mole range of about 1.2 moles to about 40 moles or more per mole of substituted succinic anhydride and a quantity of $H_2O_2$ to provide a mole range of about 2 moles to about 10 moles or more per mole of substituted succinic anhydride. In a preferred embodiment employing sulfuric acid as the strong acid reaction medium, the use of about 1.2 moles to about 10.0 moles of sulfuric acid and about 2.0 moles to about 5.0 moles of hydrogen peroxide per mole of substituted succinic anhydride precursor is particularly advantageous.

The present process can be conducted at temperatures in the range of 15° C. or less to 60° C. or more. Preferably the reaction mass is maintained in the range of about 30° to about 50° C. The reaction is exothermic and localized concentrations of the substituted succinic anhydride and/or the hydrogen peroxide reactants are to be avoided for the purposes of safety. Where the reaction is conducted at a temperature at the boiling point of the reaction modifier means of condensing the modifier and reincorporating it in the reaction mixture can be employed with good results.

Although the process can be conducted below or above atmospheric pressure, it is advantageous to carry out the process at ambient pressure.

The present process can be carried out batchwise or in a continuous manner. Good results can be obtained using a stirred tank reactor. The interior surfaces of the reactor can be of various materials, which are non-reactive with the reactor contents, such as ceramic, glass, plastic, tantalum, zirconium, stainless steel passivated by contact with Caro's acid, and the like. Interior reactor surfaces of a metal such as iron, which leave a residue in the products of reaction which subsequently accelerate the decomposition of the substituted-butanediperoxoic acid product, are to be avoided. Generally, the reactor is provided with temperature control means to maintain the desired temperature of the reactor contents such as a water jacket and the like.

The invention is further illustrated by, but not limited to, the following examples wherein all parts and percentages are by weight unless otherwise indicated.

EXAMPLE 1

A 1 liter three-neck glass flask, equipped with a Teflon paddle stirrer, thermometer and reflux condenser, and positioned in a water bath, was charged with 190 ml (281.2 grams) methanesulfonic acid, 10 grams water, 20 grams decylsuccinic anhydride and 17 ml (22.4 grams) methylene chloride. With stirring 20 ml (23.8 grams) of 50% hydrogen peroxide were slowly added over a period of 10–20 minutes and stirring was continued for an additional 40–70 minutes and the reaction mixture was maintained in the range of 38°–42° C. The reaction product precipitated upon formation. The reaction mixture was a fluid slurry throughout the reaction period and no gellation was evident. The slurry was cooled to ambient temperature, about 19° C., vacuum filtered, washed and dried to yield 21.69 grams of decylbutanediperoxoic acid (86.5% of theory). The product was analyzed for active oxygen by dissolving a 50 mg sample in 0.5 ml of acetone, adding 1.0 ml of glacial acetic acid followed by 10.0 ml of 5% KI and titrating with standard 0.1 N sodium thiosulfate solution. The sample showed 10.66% active oxygen (96.7% of theory). The product was recovered by filtering and washing the reaction mixture using a glass Buchner funnel attached to a vacuum source, 250 torr (33.3 k Pa), and washing the filter cake with 70–100 ml deionized water used to wash out the reaction flask, followed by seven additional washes with 60 ml cold deionized water.

Initial filtration was completed in about 10 minutes and all the washings were completed in less than about 1 hour. Without the presence of the methylene chloride reaction modifier, the reaction mass forms a gel of increased volume which requires an initial filtration time in excess of an hour.

EXAMPLE 2

A 500 ml three-neck flask equipped with a Teflon paddle stirrer, thermometer and reflux condenser and positioned in a water bath was charged with 80 ml (146.4 grams) 98% sulfuric acid, 20 grams water, and 20 ml (23.8 grams) 50% hydrogen peroxide. The mixture was stirred at 300 rpm and 10 grams of decylsuccinic anhydride was added. The reaction mixture was maintained at 38°–41° C. After about 10 minutes the reaction mixture gelled and foam increased total volume about 50%. Five ml (6.6 grams) of methylene chloride was added. The gel broke upon the incorporation of the methylene chloride, the stirrer speed increased to 450 rpm and the reaction mixture returned to its initial volume providing a fluid slurry. Stirring was continued for about 40 minutes then the condenser was removed to allow the methylene chloride to evaporate out of the reactor. The reaction mixture, cooled to ambient temperature, about 20° C., was vacuum filtered, washed and dried. Initial filtration was complete in about 12 minutes. Yield of decylbutanediperoxoic acid product was 10.1 grams (81.7% of theory) having an active oxygen content of 10.7% (97% of theory).

EXAMPLE 3

The general procedures and techniques of Example 1 were employed except that 18 grams of octylsuccinic anhydride was used in place of the decylsuccinic anhydride in the presence of 15 ml (19.8 grams) methylene chloride and the reaction was conducted at 38°–42° C. for about 1 hour. No gel was evident in the reaction mixture and the product was readily filtered, washed and dried to yield 14.54 grams of octylbutanediperoxoic acid (62.3% of theory) having an active oxygen content of 11.87% (97.3% of theory).

EXAMPLE 4

The general procedures and techniques of Example 1 were employed except that 22.3 grams of dodecylsuccinic anhydride was used in the presence of 15 ml (19.8 grams) of methylene chloride and the reaction was conducted at 42°–45° C. for about 1 hour. No gel was evident in the reaction mixture and the product was readily filtered, washed and dried to yield 26.31 grams of dodecylbutanediperoxoic acid (85.5% of theory) having an active oxygen content of 8.68% (86% of theory).

EXAMPLE 5

The general procedures and techniques of Example 1 were employed except that 15 ml (22.5 grams) of trichloromethane was used in place of the 17 ml of methylene chloride as reaction modifier. The reaction was conducted at 38°–42° C. for about 1 hour. No gel was evident in the reaction mixture and the product was readily filtered, washed and dried to yield 20.18 grams of decylbutanediperoxoic acid (78% of theory) having an active oxygen content of 10.17% (92% of theory).

EXAMPLE 6

The general procedures and techniques of Example 1 were employed except that 15 ml (12.9 grams) of 2-chloropropane were used in place of the 17 ml of methylene chloride as reaction modifier. The reaction was maintained at 42°–45° C. for about 1 hour. No gel was evident in the reaction mixture and the product was readily filtered, washed and dried to yield 20.00 grams of decylbutanedeperoxoic acid (79.9% of theory) having an active oxygen content of 10.64% (96.5% of theory).

The following Examples illustrate the advantages of the present invention to obtain higher production rates.

EXAMPLE 7

Employing the general procedures and techniques of Example 2, decylbutanediperoxoic acid was prepared, using 3.7 moles $H_2O_2$ and 6.8 moles $H_2SO_4$ per mole of succinic anhydride, by charging to the flask 140 ml (256.2 grams) 98% sulfuric acid, 80 ml (95.2 grams) 50% hydrogen peroxide and 45 ml (59.4 grams) methylene chloride. With stirring at 300 rpm, 90 grams of decylsuccinic anhydride were added and the reaction mixture was maintained at 40° C. for 30 minutes then cooled to ambient temperature, about 23° C. No gel was evident in the reaction mixture which was a fluid thick slurry and was vacuum filtered, washed four times by reslurrying in cold deionized water and dried.

Initial filtration was complete in about 30 minutes. Yield of decylbutanediperoxoic acid product was 105.5 grams (97% of theory) having an active oxygen content of about 10.9% (98% of theory).

EXAMPLE 8

Employing the general procedures and techniques of Example 2, decylbutanediperoxoic acid was prepared, using 2.4 moles $H_2O_2$ and 4.4 moles $H_2SO_4$ per mole of succinic anhydride, by charging to the reaction flask 70 ml (128.1 grams) 98% sulfuric acid, 40 ml (47.6 grams) 50% hydrogen peroxide and 70 ml (92.4 grams) methylene chloride. With stirring at 300 rpm, 70 grams of decylsuccinic anhydride were added and the reaction mixture was maintained at 40° C. for about one hour then cooled to about 15° C. No gel was evident in the reaction mixture which was vacuum filtered and the filter cake was washed four times and dried. Initial filtration was complete in about 9 minutes. Yield of decylbutanediperoxoic acid was 77.8 grams (90% of theory) having an active oxygen content of about 10.7% (97% of theory).

The advantages of the use of small amounts of the water-immiscible reaction modifier in accordance with this invention is particularly surprising in view of the results obtained employing the process and procedures described in U.S. Pat. No. 4,172,086 issued Oct. 23, 1979 to Sidney Berkowitz. For example, the procedure described in example 2 of U.S. Pat. No. 4,172,086 was employed using 20.54 grams of decylsuccinic anhydride, 203 ml (268 grams) methylene chloride, 25 grams of 98% sulfuric acid and 13.4 ml (15.5 grams) 50% hydrogen peroxide. Based on the active oxygen content of the decylbutanediperoxoic acid product the yield was about 15% compared to the present Examples employing about one tenth the amount of methylene chloride providing a yield of greater than 80%.

Various means can be employed to recover the product of the present process. For example, the product can be isolated from the reaction mixture by solid liquid separation such as decantation, filtration, centrifugation and the like, or by solvent extraction using water-immiscible hydrocarbon or halogenated hydrocarbon solvents for the substituted-butanediperoxoic acid and recrystallization of the product. Recovery of the product by filtration in conjunction with sufficient washings is particularly advantageous.

The substituted-butanediperoxoic acids prepared by the process of this invention are particularly useful as the active component in bleach compositions used in laundrying fabrics.

Such diperoxoic acids can be formulated with suitable stabilizers to prevent exothermic decomposition, such as materials which are capable of liberating moisture at a temperature below the decomposition temperature of the particular substituted-butanediperoxoic acid compound. A wide variety of suitable exotherm control materials can be used and include hydrated materials such as potassium aluminum sulfate dodecahydrate, magnesium ammonium sulfate hexahydrate, acids, such as boric acid, malic acid, maleic acid, succinic acid, substituted-succinic acids, azalaic acid, dodecanedioic acid, cyclohexane dicarboxylic acid and the like. Boric acid is preferred.

Suitable stabilizers to prevent catalytic decomposition of the diperoxoic acids in the presence of heavy metals, for example, iron and copper, are chelating agents. Suitable chelating agents are alkali metal polyphosphates, ethylenediamine tetra acetic acid, 1-hydroxy-ethylidene diphosphonic acid, aminotri (methylenephosphonic acid), ethylenediaminetetra (methylenephosphonic acid), diethylenetriaminepenta (methylenephosphonic acid), phosphoric acid and mixtures thereof. Phosphoric acid or a mixture of phosphoric acid and tetrasodium pyrophosphate is preferred. The presence of the chelating agents also serves to enhance the bleaching properties of the diperoxoic acids under laundry use conditions.

In addition to the chelating agents and exotherm control agents mentioned above, coating or encapsulation materials can also be used to extend the shelf life of dry formulations containing the substituted-butanediperoxoic acids as the primary bleaching agent. Suitable coating materials include a wide variety of fatty acids, fatty alcohols, derivatives thereof, such as ethers and esters, derivatives of polyethylene glycols, such as esters and ethers, hydrocarbon oils, waxes and the like. These materials aid in preventing moisture from reaching the diperoxoic acid or can be used to segregate the compound from other agents which may be present and adversely affect the diperoxoic acid's stability in the formulation. Other agents can include additional detergent materials such as surfactants, builders, antistatic agents, coloring agents, bleach activators, perfumes and the like.

A diluent can be employed as a processing aid to adjust the concentration of the diperoxoic acid as the primary bleaching agent in the formulating, shipping and subsequent addition to the wash water or blending with additional agents. The diluent or processing aid can be used in an amount to provide a formulation containing from about 10 to 60 percent by weight of the active substituted-butanediperoxoic acid, from about 1 to 5 percent by weight chelating agent, from about 15 to 55 percent by weight exotherm control agent. A preferred diluent is sodium sulfate which is compatible with the stabilizers as well as ingredients in detergent formulations.

The use of concentrated sulfuric acid as the reaction medium in the process of the present invention is compatible with and facilitates the processing of the substituted-butanediperoxoic acid into bleach formulations. For example, minor amounts of sulfuric acid retained in the filter cake of the product produced by the present invention can be neutralized with a borax wash to provide some of the boric acid and sodium sulfate useful in producing the bleach formulations containing the substituted-butanediperoxoic acid product as the active agent.

Alternatively, a substantial amount of the sulfuric acid in the resultant reaction slurry can be neutralized with borax prior to filtration to obtain upon filtration a suitable particulate mixture of substituted-butanediperoxoic acid, boric acid and sodium sulfate. In this manner, the active substituted-butanediperoxoic acid is recovered in admixture with boric acid and sodium sulfate which aids in subsequent handling and formulation of the product as a bleach.

Although the invention has been described in terms of specified embodiments which are set forth in considerable detail, it should be understood that this is by way of illustration only and that the invention is not necessarily limited thereto since alternative embodiments in operating techniques will become apparent to those skilled in the art in view of the present disclosure. Accordingly, modifications are contemplated which can be made without departing from the spirit of the described invention.

What is claimed is:

1. A process for making alkyl or phenyl substituted-butane diperoxoic acid which comprises reacting hydrogen peroxide with alkyl or phenyl substituted succinic anhydride in a strong acid reaction medium and in the presence of a water immiscible reaction modifier in the range from about 0.25 ml. to about 2 ml. of said modifier per gram of said anhydride, said amount of modifier being sufficient to prevent a gelled reaction mass and substantially less than required to dissolve the alkyl or phenyl substituted-butane diperoxoic acid.

2. The process of claim 1 wherein the substituted succinic anhydride is of the general formula

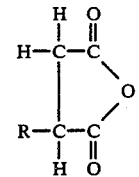

wherein R is alkyl of 6 to 18 carbon atoms or phenyl.

3. The process of claim 1 wherein the reaction modifier is a hydrocarbon.

4. The process of claim 3 wherein the reaction modifier is a halogenated hydrocarbon having a boiling point in the range of about 5° to about 100° C.

5. The process of claim 1 wherein the strong acid is sulfuric acid, methanesulfonic acid, ethanesulfonic acid, butanesulfonic acid, fluoromethanesulfonic acid or trifluoromethanesulfonic acid.

6. The process of claim 5 wherein the strong acid is sulfuric acid or methanesulfonic acid and the reaction modifier is a halogenated hydrocarbon having a boiling point in the range of about 25° to about 65° C.

7. The process of claim 6 wherein the strong acid reaction medium is aqueous sulfuric acid of about 75% to about 90% by weight sulfuric acid.

8. The process of claim 7 wherein the substituted succinic anhydride is decylsuccinic anhydride.

9. The process of claim 7 wherein the substituted succinic anhydride is octylsuccinic anhydride.

10. The process of claim 7 wherein the substituted succinic anhydride is dodecylsuccinic anhydride.

11. The process of claim 7 wherein the reaction is conducted at a temperature in the range of about 15° to about 60° C.

12. The process of claim 7 wherein the reaction is conducted with about 2 moles to about 10 moles of hydrogen peroxide per mole of succinic anhydride in a reaction medium containing from about 1.2 moles to about 10 moles of sulfuric acid per mole of succinic anhydride and at a temperature in the range of about 30° to about 50° C.

* * * * *